US007364852B2

(12) United States Patent
Rouleau et al.

(10) Patent No.: US 7,364,852 B2
(45) Date of Patent: *Apr. 29, 2008

(54) SHORT GCG EXPANSIONS IN THE PAB II GENE FOR OCULOPHARYNGEAL MUSCULAR DYSTROPHY AND DIAGNOSTIC THEREOF

(75) Inventors: Guy A. Rouleau, Montreal (CA); Bernard Brais, Outremont (CA)

(73) Assignee: McGill University, Montreal (CA)

( * ) Notice: Subject to any disclaimer, the term of this patent is extended or adjusted under 35 U.S.C. 154(b) by 461 days.

This patent is subject to a terminal disclaimer.

(21) Appl. No.: 10/889,263

(22) Filed: Jul. 12, 2004

(65) Prior Publication Data

US 2005/0069922 A1 Mar. 31, 2005

Related U.S. Application Data

(63) Continuation of application No. 09/590,211, filed on Jun. 8, 2000, now Pat. No. 6,828,430, which is a continuation of application No. PCT/CA98/01133, filed on Dec. 7, 1998.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3

(58) Field of Classification Search ............... 435/6; 536/23.1, 24.3

See application file for complete search history.

(56) References Cited

U.S. PATENT DOCUMENTS 6,828,430 B1 12/2004 Rouleau et al.

FOREIGN PATENT DOCUMENTS

WO WO98/31800 7/1998
WO WO99/29896 6/1999

OTHER PUBLICATIONS

GenBank Accession No. U93050 (Sep. 1997) and X89969 (Nov. 1995).*
Robinson et al., 2005, Hum Genet 116: 267-271.*
Bae et al., 2007, J of Clinical Neuroscience 14: 89-92.*
Akarsu, A.N., et al., "Genomic Structure of HOXD13 Gene: A Nine Polyalanine Duplication Causes Synpolydactyly in Two Unrelated Families," *Human Molecular Genetics*, 5(7): 945-952 (1996).
Bienroth, S, et al., "Assembly of a Processive Messenger RNA Polyadenylation Complex," *The EMBO Journal*, 12(2): 585-594 (1993).
Bouchard, J.P. et al., "A Simple Test for the Detection of Dysphagia in Members of Families with Oculopharyngeal Muscular Dystrophy (OPMID)," Can.J. Neurol. Sci. 19(2):296-297 (1992).

Brais, B., et al.,"Using the Full Power of Linkage Analysis in 11 French Canadian Families to Fine Map the Oculopharyngeal Muscular Dystrophy Gene," *Neuromuscular Disorder* 7(1):S70-S74 (1997).
Brais, B, et al., "The Oculopharyngeal Muscular Dystrophy Locus Maps to the Region of the Cardiac α and β Myosin Heavy Chain Genes on Chromosome 14q11.2-q13," *Human Molecular Genetics*, 4(3): 429-434 (1995).
Brais, B., et al., "Short GCG Expansions in the PABP2 Gene Cause Oculopharyngeal Muscular Dystrophy," *Nature Genetics* 18: 164-167 (1998).
Brais, B., et al., "Oculopharyngeal Muscular Dystrophy," *Seminars in Neurology* 19: 59-66 (1999).
Davies, S.W., "Formation of Neuronal Intranuclear Inclusions Underlies the Neurological Dysfunction in Mice Transgenic for the HD Mutation," *Cell*, 90:537-548 (1997).
DiFiglia, M, et al., "Aggregation of Huntingtin in Neuronal Intranuclear Inclusions and Dystrophic Neurites in Brain," *Science*, 277: 1990-1993 (1997).
Editorials, "DNA-Triplet Repeats and Neurologic Disease," *The New England Journal of Med.*, 335(16): 1222-1224 (1996).
Evans, G.A, et al., "High Efficiency Vectors for Cosmid Microcloning and Genomic Analysis," *Gene*, 79:9-20 (1989).
Forood, B., et al., "Formation of an Extremely Stable Polyalanine β-Sheet Macromolecule," *Biochem. And Biophysical Res. Communications*, 211(1): 7-13 (1995).
Genebank Deposit AF026029, Feb. 20, 1998.
Grewal, R.P., et al. "Genetic Mapping and Haplotype Analysis of Oculopharyngeal Dystrophy," *NeoroReport*, 9: 961-965 (1998).
Krause, S., et al., "Immunodetection of Poly(A) Binding Protein II in the Cell Nucleus," *Experimental Cell Res.*, 214: 75-82 (1994).
Lafrenière R.G., et al., "Unstable insertion in the 5' flanking region of the cystatin B gene is the most common mutation in progressive myoclonus epilepsy type 1, EMP1", *Nature Genetics*, 15:298-302 (Mar. 1997).
Lamartine, J. et al., "Cloning Sequencing and Chromosomal Assignment of a New cDNA Clone to Xq12-q13 and 14q11," EMBL Data Base Accession No. U12206 (1995).

(Continued)

*Primary Examiner*—Ethan Whisenant
(74) *Attorney, Agent, or Firm*—Hamilton, Brook, Smith & Reynolds, P.C.

(57) ABSTRACT

The present invention relates to a human PAB II gene containing transcribed polymorphic GCG repeat, which comprises a sequence as set forth in SEQ ID NO:3, which includes introns and flanking genomic sequence. The allelic variants of GCG repeat of the human PAB II gene are associated with a disease related with protein accumulation in nucleus, such as polyalanine accumulation, a disease related with swallowing difficulties, such as oculopharyngeal muscular dystrophy. The present invention also relates to a method for the diagnosis of a disease with protein accumulation in nucleus, which comprises the steps of: a) obtaining a nucleic acid sample of said patient; and b) determining allelic variants of GCG repeat of the gene of claim 1, and wherein long allelic variants are indicative of a disease related with protein accumulation in nucleus.

11 Claims, 8 Drawing Sheets

OTHER PUBLICATIONS

Mundlos, S., et al., "Mutations Involving the Transcription Factor CBFA1 Cause Cleidocranial Dysplasia," *Cell*, 89: 773-779 (1997).

Muragaki, Y., et al., "Polyalanine Expansion in Synpolydactyly Might Result from Unequal Crossing-Over of HOXD13," *Science* 275: 406.

"National Cancer Institute, Cancer Genome Anatomy Project (CGAP), Tumor Gene Index," EMBL Data Base Accession No. AA618589 (1997).

Nemeth, A., et al., "Isolation of Genomic and cDNA Clones Encoding Bovine Poly(A) Binding Protein II," *Nucleic Acids Res.*, 23(20): 4034-4041 (1995).

Riggins, G.J., et al. "Human Genes Containing Polymorphic Trinucleotide Repeats," *Nat Genet*, 2(3):186-191 (1992).

Rommens J.M., et al., "Towards a Transcriptional Map of the q21-q22 Region of Chromosome 7", *Plenum Press*, pp. 65-79 (1994).

Scherzinger, E., et al., "Huntingtin-Encoded Polyglutamine Expansions Form Amyloid-Like Protein Aggregates In Vitro and In Vivo," *Cell* 90: 549-558 (1997).

Stajich, J.M., et al., "Confirmation of Linkage of Oculoparyngeal Muscular Dystrophy to Chromosome 14q11.2-q13 in American Families Suggests the Existence of a Second Casual Mutation," *Neuromuscular Disorders*, 7: S75-S81 (1997).

Sullivan, T.B.T., et al., "Oculopharyngeal Muscular Dystrophy (OPMD)-Report and Genetic Studies of an Australian Kindred," *Clinical Genetics*, 51: 52-55 (1997).

Tome, M.S., et al., "Nuclear Inclusions in Oculopharyngeal Dystrophy," *Act Neuropathol.* 49: 85-87 (1980).

Wahle, E., et al., "Mammalian Poly(A)-Binding Protein II," *J. of Biological Chem.*, 268(4): 2937-2945 (1993).

Wahle E., "A Novel Poly(A)-Binding Protein Acts As a Specificity Factor in the Second Phase of Messenger RNA Polyadenylation," *Cell*, 66: 759-768 (1991).

Wells, R.D.,"Molecular Basis of Genetic Instability of Triplet Repeats," *The Journal of Biological Chem.* 271(6): 2875-2878 (1996).

\* cited by examiner

GATC  FIG. 2G

OPMD dominant mutations:

N: ATGGGCGGCGGCGGCGGCGGCAGCAGCA
   ATGGGCGGCGGCGGCGGCGGCGG(GCG)$_{2-7}$GCA

Polyalanine insertions:

N: MAAAAAAAAGAAGGRGS
   MAAAAAA(A)$_{2-7}$AAAAGAAG

FIG. 3

```
   1 aatgaaggtg gacacccaaa tagcccccaat acaaatgcct gttcaatcaa ccaaacatct
  61 aagcagcaca tctatgtggt agcatattgc caggccgtga gactgcgaat ataaatagga
 121 accgccctc atctgcaggc gctcacaacc tagttagcaa acagtaaaac aattaagcgc
 181 gccgtggaca taggcccact tgtcctggga aatgagggga agctggggtt tgcagtggtt
 241 tgattgaagg gggactacat gttagaggca cagactgggt gcaggtacac ccaaaggaac
 301 gagaagagtg gaaggaaaca acatccacaa agtaaccaca tgctggcgta tcgaaggccg
 361 tgatttacgg ttttgagact ttacctcgcc agcaaagggg ggccagtctg ttagcggtgc
 421 agattggagg ggtgacattg gaagctgtcc aggaaaaaga aaatggaact ggggagcaga
 481 aggcctacgc aagagggcgg gacagacagg acttgtgact agtagctctg gactgaggaa
 541 tcctccctgc tttctggtgc gggagagcta gtggatgatg gtgccaataa cctgatggg
 601 gaaagtaagc tccctcctgg aatgcttcat tcacaacctc catttcagc aacatcccat
 661 ctactggtgc ttcctggtcg agatacaagt ttcctgaaac tgctgctctg ttttgggcct
 721 caccgggcca acagctcact agctggcaag cagtagtatc aagatggcgg cccctagga
 781 ctggctagtc atgtgacctc gggtttccca agtttgaagc ccggcagtcc tttcggggc
 841 aaggttcacc tgtcacgaaa cgagtgtcac cccttcgact ctcgcaagcc aatcggcatc
 901 tgagactggg ccactgcggt gaggcgatcg gaagattggt cctttccagt cgcctagcta
 961 gggccaatca cggagcgtcc catacttcgc gggcccgccc gtaggccggg gagaagcagg
1021 aatatcgtca cagcgtggcg gtattattac ctaaggactc gataggaggt gggacgcgtg
1081 ttgattgaca ggcagatttc cctaccggga tttgagaatt tggcgcagtg cccgcccttag
1141 aggtgcgctt atttgattgc caagtaatat tccccaatgg agtactagct catggtgacg
```

FIG. 4A

```
1201  ggcaggcagc  ttgagctaat  gagtcctccg  tggccggcgc  agctctccac  atgccggggcg
1261  gcgggcccca  gtctgagcgg  cgatggcggg  ggcggcggca  gcggcagcag  cagcggggc
1321  tgcgggcggt  cgggctccg   ggccggggcg  gcggcgccat  cttgtgcccg  ggccggtgg
1381  ggaggccggg  gagggggccc  cgggggggcgc  aggggactac  gggaacggcc  tggagtctga
1441  ggaactggag  cctgaggagc  tgctgctgga  gcccgagccg  gagcccgagc  ccgaagagga
1501  gccgccccgg  ccccgcgccc  cccggggagc  gccctggccct  gggcctggtt  cgggagcccc
1561  cggcagccaa  gaggaggagg  aggagccggg  actggtcgag  ggtgacccgg  gggacggcgc
1621  cattgaggac  ccggtgagga  aggagggcga  gcgagcaggc  cggcggctgg  cgcgtcactg
1681  gaggcccaga  gctcggggcga  gcggtggcag  gcgggggtg   gggttgggcg  gggaataacg
1741  tggctggggc  gggtcgggcc  cagcgatcac  tacaaggggc  ccgactggct
1801  tgattcgggc  gtcacgggtg  cctagtgttg  ttctagagag  ggtagctttt  ctttatcac
1861  gaccctcgca  tggggcgagg  gaaatggccg  agcatggctg  aggcgcgctc  tggccgagag
1921  cagggcacag  ccctgcgtt   ggttcctctt  aagctgtcct  ccatacctc   cccacttata
1981  ttaggagctg  gaagctatca  aagctcgagt  caggagaatg  gaggaagaag  ctgagaagct
2041  aaaggagcta  cagaacgagg  tagagaagca  gatgaatatg  agtccacctc  caggcaatgc
2101  tgagtaactg  gcggttgcac  gcggagcccg  ggttctcggg  ttgaagggt   tgtggggagg
2161  atgggggaatg  tggggttaga  tactcggcac  cctgagctg   cttgtctgag  ctattatgac
2221  tgtgccgcgg  tcatagtccg  ttgtgtgttc  ctctgacctt  tgtgaggcag  aactgatatt
2281  ttgttggtgg  tagccttgtg  tagcctttg   cctcccttg   attgtgttgc  tctttattct
2341  tagtctacgt  ctatctttct  ttggtagagg  ttgcgtgctc  gcatttgacc  ttcaaatcta
```

FIG. 4B

```
2401 atagtttttc ctccaattgg agacgcttta ggattctaag agaaagcaag ctggaagggg
2461 tttcccttt aaattctaga aatgtggagt ctcagcccac ttaattttgc tcactcttaa
2521 aagcatttca accaaagcca ttcattaggg atttgatttg gagggcagga gggattccta
2581 tactgttta agtgtgtatt aattctttca atttatcgaa ttattagtg agtaacctgc
2641 tatgcactag gcactattct cggcttgtgg gtacagcagg gaacagcaca gaccaaaatc
2701 tttgccttca ctgagcttat gggatagtgc tggtggtgga agtgcaacat attggtcaag
2761 tagaaaacaa gtgtgtggtt tttgtaaaaa attatttttt cctgatagct ggcccggtga
2821 tcatgtccat tgaggagaag atggaggctg atgcccgttc catctatgtt ggcaatgtga
2881 cgtactgggg ctctgactgg ggttgggggc aagttcttct tttgggaat tatttaatag
2941 tcctgaaaga acatctccgg gatagatgtg gtttttgggtg tgaggggagt gtgggaagga
3001 ggttaaaggt aatggaatga tcagtaatca gcaaaggctc gctttggtgt agaccaaagg
3061 attaattcct caaattacca gattcatgt gcctggtgcc atgatgccc ttctcctctc
3121 ctcgggaggg ttctttgag acagaaatt gcctgtgtgcc tgtgaatt ttctcctctc
3181 atcaggtgga ctatggtgca acagcagaag agctggaagc tcactttcat ggctgtggtt
3241 cagtcaaccg tgttaccata ctgtgtgaca aatttagtgg ccatcccaaa ggtaaagtaa
3301 aggggagtaa gttgagataa tttaaattac agtgtacaaa tagataaatt atgttttata
3361 ttgagcagta agttatttgg tgttaacaca ggtgatctgt gtcatttaag atcatggcat
3421 taatgttgat atatcaggag ttgcacctaa atgtcttcag aggccagata acaaaaatga
3481 aggctagatg tggtgggat tacgaactag aaggggaggg gcagcttcta cttggcctat
3541 tatggcatat ggaaattcag gccctgtgtg tcttatttt acaaatttca aagagtagct
```

FIG. 4C

```
3601  ggaaattta  aaatttaaat  gatttcgaat  gattgaaatt  ttccatttag  aagaattttg
3661  acaaataaaa  aatataactg  cattgtagcc  caaaacgaag  catgcctgca  ggttgaattt
3721  gacctgtgag  gtatttgtaa  cctcagagag  atacaatgac  aattcttttc  aggtttgcgt
3781  atatagagtt  ctcagacaaa  gagtcagtga  ggacttcctt  ggccttagat  gagtccctat
3841  ttagaggaag  gcaaatcaag  gtaagcctat  gtccattgct  gttctagttg  tgtataaact
3901  ctccaggttg  cctttaaggc  tatcatttgt  tcatctctga  ctcaggtgat  cccaaaacga
3961  accaacagac  caggcatcag  cacaacagac  cgggttttc   cacgagcccg  ctaccgcgcc
4021  cggaccacca  actacaacag  ctcccgctct  cgattctaca  gtggttttaa  cagcaggccc
4081  cgggtcgcg   tctacaggtc  aggatagatg  ggctgctcct  ctttccccg   cctcccgtga
4141  gccccgtatg  cttcctcctc  tctggtctga  ggaacctccc  tccccccacc  cctcccgtg
4201  gtcttcagga  actttgtctc  ctgcctgtgc  aggttgagga  aggtagttgc  aggccaggcc
4261  agaaggcagc  ctcatcatct  tttctgcagt  agaaattggt  gataaggct   gcatccctcc
4321  cttggttcaa  agaggcttcc  acccccagcc  tttttttct   tgggagttgg  tggcatttga
4381  aggtgtttgc  ggacaaaact  gggaggaaca  ggcctccag   gaagttgaaa  gcactgcttg
4441  gacatttgtt  acttttttcg  gagttaggga  gggattgaag  actgaacctc  cccttggaaga
4501  ataccagagg  ctagctagtt  gatcctccca  acagccttgt  gggaggattt  tgagatactt
4561  attctttatt  tgagccagtc  ttgcaaggtt  aacttctcac  tgggcctagt  gtggtnccca
4621  ggtttttgcc  ttgcttcact  tctgtctcta  catttaaata  gacgggttag  gcatataaac
4681  cttggctttt  cataagctct  acctgcctat  cccaggagt   taggaggat   ctatttgtga
4741  aggccctagg  gtttaaaaac  tgtggaggac  gataaaaagg  tgaaaaactg  gggtcctttt
```

FIG. 4D

```
4801 ccttgcccct gtctctcact cagatgcgct tcttttcgc cactgttttgg caaagtttttc
4861 tgttaagccc ccctcccct gccccagttc tccagtgc gttactattt ctgggatcat
4921 ggggtcggtt ttaggacact tgaacacttc ttttccccc ttcccttcac agtaactggg
4981 gcagggcct acgggaggg gcttgtactg aactatctag tgatcacgtt aacacctaac
5041 tctcctttctt tcttccaggg gccggctag agcgacatca tggtattccc cttactaaaa
5101 aaagtgtgta ttaggaggag agagaggaaa agaaggaaa aaaaaagaat
5161 taaaaaaaaa aaaagaaaa acagaagatg acctttgatgg aaaaaaaata ttttttaaaa
5221 aaaagatata ctgtggaagg gggagaatc ccataactaa ctgctgagga gggacctgct
5281 ttggggagta ggaaggcc caggagtgg ggcaggggc tgcttattca ctctggggat
5341 tcgccatgga cacgtctcaa ctgcgcaagc tgcttgccca tgtttccctg ccccttcac
5401 cccttgggc ctgctcaagg gtaggtggc gtggtggta ggagggtttt ttttacccag
5461 ggctctgaa ggacaccaaa ctgttctgct tgttaccttc cctccgtct tctcctcgcc
5521 tttcacagtc ccctcctgcc cagccaggtc taccaccac cccaccctc
5581 tttctccggc tcccctgcccc tccagattgc ctgtgatct atttttgttc ctttttgtgtt
5641 tctttttctg ttttgagtgt ctttctttgc aggttctgt agccgaaga tctccgttcc
5701 gctcccagcg gctccagtgt aaattccct tcccctggg gaaatgcact accttgtttt
5761 gggggttta gggtgttt tgttttcag tgttttgtt tttttgttt tttttttcc
5821 tttgcctttt ttccctttta tttggagga atgggaggaa gtgggaacag ggaggtggga
5881 ggtggattt gtttatttt ttagctcatt tccaggggtg ggaatttttt tttaatatgt
5941 gtcatgaata aagttgttt tgaaaataaa aaaaaaaaaa aaaaaaaaaa aaaaaaaaaa
6001 aa
```

FIG. 4E

SHORT GCG EXPANSIONS IN THE PAB II GENE FOR OCULOPHARYNGEAL MUSCULAR DYSTROPHY AND DIAGNOSTIC THEREOF

RELATED APPLICATIONS

This application is a continuation of U.S. application Ser. No. 09/590,211, filed Jun. 8, 2000, now U.S. Pat. No. 6,828,430 which is a continuation of International Application No. PCT/CA98/01133, which designated the United States and was filed Dec. 7, 1998, published in English, which claims priority to Canadian Patent No. 2,218,199, filed Dec. 9, 1997.

The entire teachings of the above applications are incorporated herein by reference.

BACKGROUND OF THE INVENTION

1. Field of the Invention

The invention relates to PAB II gene, and its uses thereof for the diagnosis, prognosis and treatment of a disease related with protein accumulation in nucleus, such as oculopharyngeal muscular dystrophy.

2. Description of Prior Art

Autosomal dominant oculopharyngeal muscular dystrophy (OPMD) is an adult-onset disease with a world-wide distribution. It usually presents itself in the sixth decade with progressive swallowing difficulties (dysphagia), eye lid drooping (ptosis) and proximal limb weakness. Unique nuclear filament inclusions in skeletal muscle fibers are its pathological hallmark (Tome, F.M.S. & Fardeau, Acta Neuropath. 49, 85-87 (1980)). Using the full power of linkage analysis in eleven French Canadian families, the oculopharyngeal muscular dystrophy gene was fine mapped on human chromosome 14 (Brais et al., 1997, Neuromuscular Disorders 7 (Suppl.1):S70-74). A region of 0.75 cM was thereby identified as a region containing the potential and unknown OPMD gene (Brais et al., 1997, supra). Unfortunately, the OPMD gene has yet to be isolated and its nucleic acid or protein sequence have yet to be cribbed.

It would be highly desirable to be provided with a tool for the diagnosis, prognosis and treatment of a disease related with polyalanine accumulation in the nucleus, such as observed in oculopharyngeal muscular dystrophy.

SUMMARY OF THE INVENTION

One aim of the present invention is to provide a tool for the diagnosis, prognosis and treatment of a disease related with polyalanine accumulation in nucleus, such as oculopharyngeal muscular dystrophy.

Herein, the poly(A) binding protein II (PAB II) gene was isolated from a 217 kb candidate interval in chromosome 14q11. A (GCG)6 repeat encoding a polyalanine tract located at the N-terminus of the protein was expanded to (GCG)8-13 in the 144 OPMD families screened. More severe phenotypes were observed in compound heterozygotes for the (GCG)9 mutation and a (GCG)7 allele found in 2% of the population, whereas homozygosity for the (GCG)7 allele leads to autosomal recessive OPMD. Thus the (GCG)7 allele is an example of a polymorphism which can act as either a modifier of a dominant phenotype or as a recessive mutation. Pathological expansions of the polyalanine tract may cause mutated PAB II oligomers to accumulate as filament inclusions in nuclei.

In accordance with the present invention there is provided a human PAB II gene containing a transcribed polymorphic GCG repeat, which comprises a sequence as set forth in FIG. 4, which includes introns and flanking genomic sequence.

The allelic variants of GCG repeat of the human PAB II gene are associated with a disease related with protein accumulation in the nucleus, such as polyalanine accumulation, or with a disease related with swallowing difficulties, such as oculopharyngeal muscular dystrophy.

In accordance with the present invention there is also provided a method for the diagnosis of a disease associated with protein accumulation in the nucleus, which comprises the steps of:

a) obtaining a nucleic acid sample of said patient; and b) determining allelic variants of a GCG repeat of the human PAB II gene; thereby long allelic variants are indicative of a disease related with protein accumulation in the nucleus, such as polyalanine accumulation and oculopharyngeal muscular dystrophy.

The long allelic variants have from about 245 to about 263 bp in length.

In accordance with the present invention there is also provided a non-human mammal model for the human PAB II gene, whose germ cells and somatic cells are modified to express at least one allelic variant of the PAB II gene and wherein said allelic variant of the PAB II is being introduced into the mammal, or an ancestor of the mammal, at an embryonic stage.

In accordance with the present invention there is also provided a method for the screening of therapeutic agents for the prevention and/or treatment of oculopharyngeal muscular dystrophy, which comprises the steps of:

a) administering the therapeutic agents to the non-human animal of the present invention or oculopharyngeal muscular dystrophy patients; and b) evaluating the prevention and/or treatment of development of oculopharyngeal muscular dystrophy in this animal (such as a mammal) or in patients.

In accordance with the present invention there is also provided a method to identify genes-products thereof, or part thereof, which interact with a biochemical pathway affected by the PAB II gene, which comprises the steps of:

a) designing probes and/or primers using the PAB II gene and screening oculopharyngeal muscular dystrophy patients samples with said probes and/or primers; and b) evaluating the role of the identified gene in oculopharyngeal muscular dystrophy patients.

BRIEF DESCRIPTION OF THE DRAWINGS

FIGS. 2A-2G illustrate the OPMD (GCG)n expansion sizes and sequence of the mutation site (SEQ ID NOS:4-9);

FIG. 3 illustrates the age distribution of swallowing time (st) for French Canadian OPMD carriers of the (GCG)9 mutation; and FIGS. 4A-4E illustrate the nucleotide sequence of human poly(A) binding protein II (hPAB II) (SEQ ID NO:3).

DETAILED DESCRIPTION OF THE INVENTION

Figure 1A:
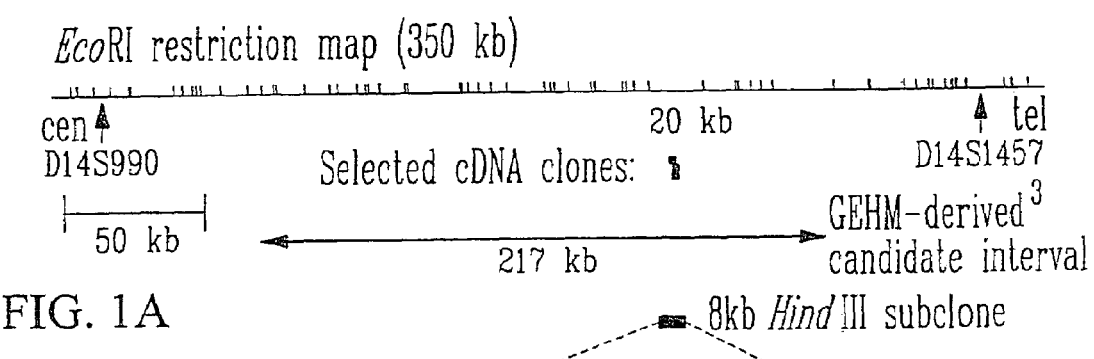
FIGS. 1A-1B illustrate the positional cloning of the PAB II gene.

In order to identify the gene mutated in OPMD, a 350 kb cosmid contig was constructed between flanking markers D14S990 and D14S1457 (FIG. 1A). Positions of the PAB II-selected cDNA clones were determined in relation to the EcoRI restriction map and the Genealogy-based Estimate of Historical Meiosis (GEHM)-derived candidate interval (Rommens, J. M. et al., in Proceedings of the third international workshop on the identification of transcribed sequences (eds. Hochgeschwender, U. & Gardiner, K.) 65-79 (Plenum, New York, 1994)).

The human poly(A) binding protein II gene (PAB II) is encoded by the nucleotide sequence as set forth in FIG. 4.

Twenty-five cDNAs were isolated by cDNA selection from the candidate interval (Rommens, J. M. et al., in Proceedings of the third international workshop on the identification of transcribed sequences (eds. Hochgeschwender, U. & Gardiner, K.; 65-79; Plenum, New York, 1994). Three of these hybridized to a common 20 kb EcoRI restriction fragment and showed high sequence homology to the bovine poly(A) binding protein II gene (bPAB II) (FIG. 1A). The PAB II gene appeared to be a good candidate for OPMD because it mapped to the genetically defined 0.26 cM candidate interval in 14q11 (FIG. 1A), its mRNA showed a high level of expression in skeletal muscle, and the PAB II protein is exclusively localized to the nucleus (Krause, S. et al., Exp. Cell Res. 214, 75-82 (1994)) where it acts as a factor in mRNA polyadenylation (Whale, E., Cell 66, 759-768 (1991); Whale, E. et al., J. Biol. Chem. 268, 2937-2945 (1993); Bienroth, S. et al., EMBO J. 12, 585-594 (1993)).

Figure 1B:
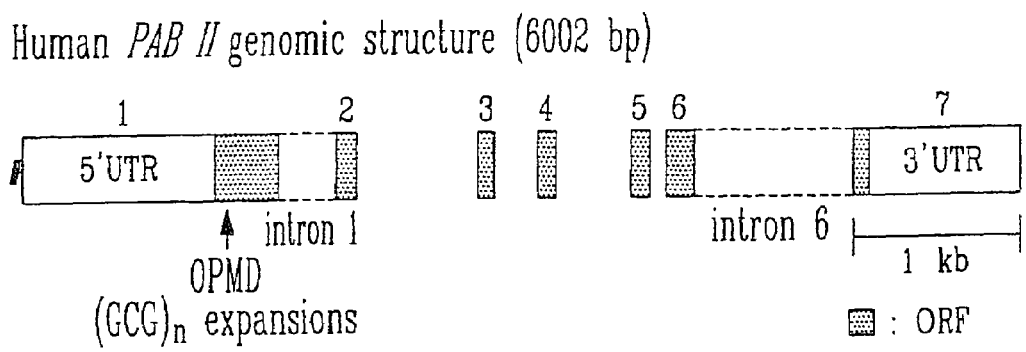

A 8 kb HindIII genomic fragment containing the PAB II gene was subcloned and sequenced (6002 bp; GenBank: AF026029) (Nemeth, A. et al., Nucleic Acids Res. 23, 4034-4041 (1995)) (FIG. 1B). Genomic structure of the PAB II gene, and position of the OPMD (GCG)n expansions. Exons are numbered. Introns 1 and 6 are variably present in 60% of cDNA clones. ORF, open reading frame; cen, centromere and tel, telomere.

The coding sequence was based on the previously published bovine sequence (GenBank: X89969) and the sequence of 31 human cDNAs and ESTs. The gene is composed of 7 exons and is transcribed in the cen-qter orientation (FIG. 1B). Multiple splice variants are found in ESTs and on Northern blots (Nemeth, A. et al., Nucleic Acids Res. 23, 4034-4041 (1995)). In particular, introns 1 and 6 are present in more than 60% of clones (FIG. 1B) (Nemeth, A. et al., Nucleic Acids Res. 23, 4034-4041 (1995)). The coding and protein sequences are highly conserved between human, bovine and mouse (GenBank: U93050). 93% of the PAB II sequence was readily amenable to RT-PCR- or genomic-SSCP screening. No mutations were uncovered using both techniques. However, a 400 bp region of exon 1 containing the start codon could not be readily amplified. This region is 80% GC rich. It includes a (GCG)6 repeat which codes for the first six alanines of a homopolymeric stretch of 10 (FIG. 2G). Nucleotide sequence of the mutated region of PAB II as well as the amino acid sequences of the N-terminus polyalanine stretch and position of the OPMD alanine insertions is also shown in FIG. 2.

Special conditions were designed to amplify by PCR a 242 bp genomic fragment including this GCG-repeat. The (GCG)6 allele was found in 98% of French Canadian non-OPMD control chromosomes, whereas 2% of chromosomes carried a (GCG)7 polymorphism (n=86) (Brais, B. et al., Hum. Mol. Genet. 4, 429-434 (1995)).

Figures 2A, 2B, 2C, 2D, 2E, 2F:

Screening OPMD cases belonging to 144 families showed in all cases a PCR product larger by 6 to 21 bp than that found in controls (FIG. 2A). (GCG)6 normal allele (N) and the six different (GCG)n expansions observed in 144 families.

Sequencing of these fragments revealed that the increased sizes were due to expansions of the GCG repeat (FIG. 2G). FIG. 2F shows the sequence of the (GCG)9 French Canadian expansion in a heterozygous parent and his homozygous child. Partial sequence of exon 1 in a normal (GCG)6 control (N), a heterozygote (ht.) and a homozygote (hm.) for the (GCG)9-repeat mutation. The number of families sharing the different (GCG)n-repeats expansions is shown in Table 1.

TABLE 1

Number of families sharing the different dominant (GCG)m OPMD mutations

| Mutations | Polyalanine† | Families |
|---|---|---|
| (GCG)8 | 12 | 4 |
| (GCG)9 | 13 | 99 |
| (GCG)10 | 14 | 19 |
| (GCG)11 | 15 | 16 |
| (GCG)12 | 16 | 5 |
| (GCG)13 | 17 | 1 |
| Total | | 144 |

†10 alanine residues in normal PAB II.

The (GCG)9 expansion shared by 70 French Canadian families is the most frequent mutation we observed (Table 1). The (GCG)9 expansion is quite stable, with a single doubling observed in family F151 in an estimated 598 French Canadian meioses (FIG. 2C). The doubling of the French Canadian (GCG)9 expansion is demonstrated in Family F151.

This contrasts with the unstable nature of previously described disease-causing triplet-repeats (Rosenberg, R. N., New Eng. J. Med. 335, 1222-1224 (1996)).

Genotyping of all the participants in the clinical study of French Canadian OPMD provided molecular insights into the clinical variability observed in this condition. The genotypes for both copies of the PAB II mutated region were added to an anonymous version of this clinical database of 176 (GCG)9 mutation carriers (Brais, B. et al., Hum. Mol. Genet. 4, 429-434 (1995)). Severity of the phenotype can be assessed by the swallowing time (st) in seconds taken to drink 80 cc of ice-cold water (Brais, B. et al., Hum. Mol. Genet. 4, 429-434 (1995); Bouchard, J.-P. et al., Can. J. Neurol. Sci. 19, 296-297 (1992)). The late onset and progressive nature of the muscular dystrophy is clearly illustrated in heterozygous carriers of the (GCG)9 mutation (bold curve in FIG. 3) when compared to the average st of control (GCG)6 homozygous participants (n=76, thinner line in FIG. 3). The bold curve represents the average OPMD st for carriers of only one copy of the (GCG)9 mutation (n=169), while the thinner line corresponds to the average st for (GCG)6 homozygous normal controls (n=76). The black dot corresponds to the st value for individual VIII. Roman numerals refer to individual cases shown in FIGS. 2B, 2D and discussed in the text. The genotype of a homozygous (GCG)9 patient and her parents is shown in FIG. 2B. Independent segregation of the (GCG)7 allele is also shown. Of note, case V has a more severe OPMD phenotype (FIG. 2D).

Figure 3:
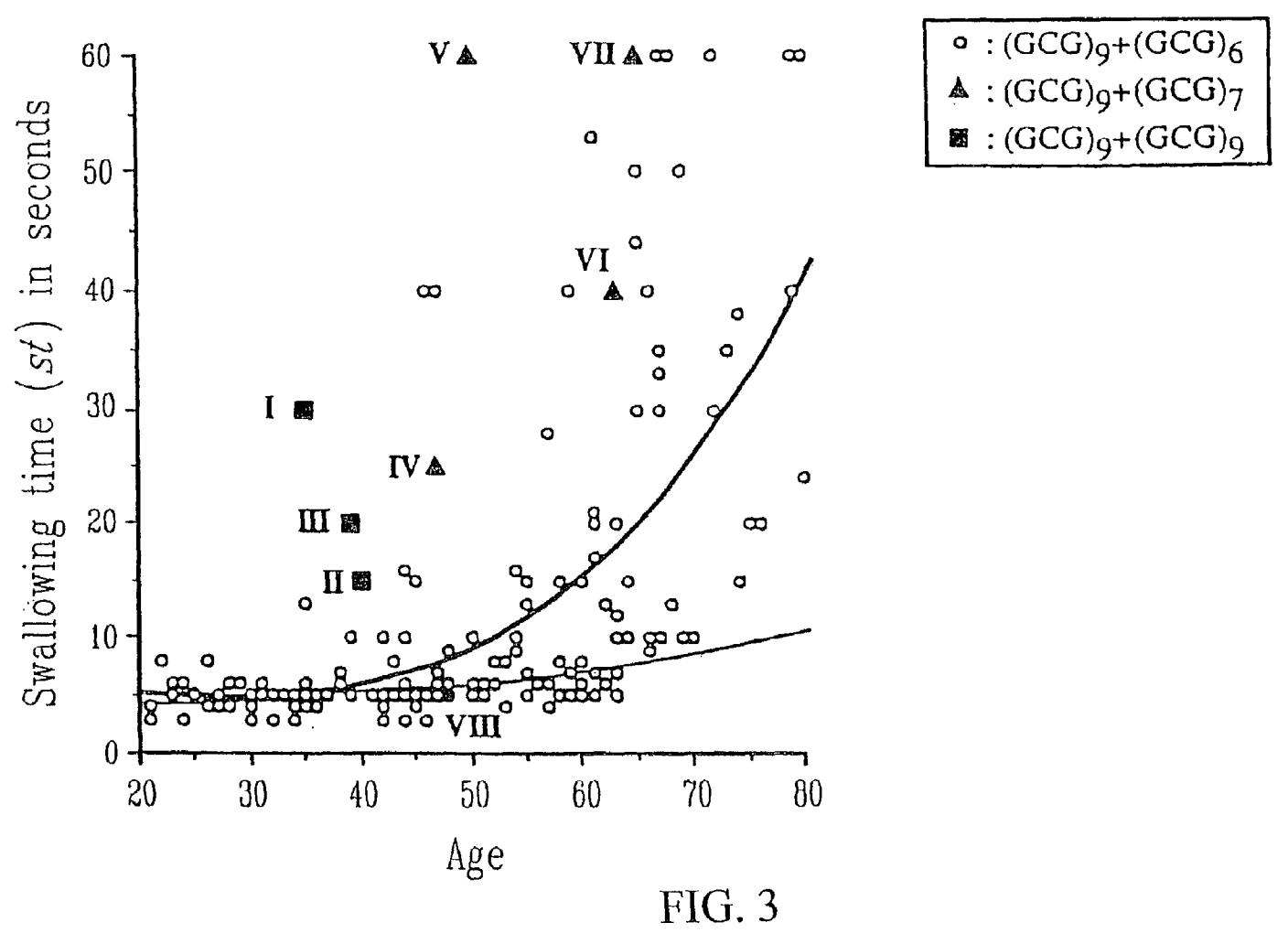

Two groups of genotypically distinct OPMD cases have more severe swallowing difficulties. Individuals I, II, and III have an early-onset disease and are homozygous for the (GCG)9 expansion (P<10-5) (FIGS. 2B, F). Cases IV, V, VI and VII have more severe phenotypes and are compound heterozygotes for the (GCG)9 mutation and the (GCG)7 polymorphism (P<10-5). In FIG. 2D the independent segregation of the two alleles is shown. Case V, who inherited the French Canadian (GCG)9 mutation and the (GCG)7 polymorphism, is more symptomatic than his brother VIII who carries the (GCG)9 mutation and a normal (GCG)6 allele (FIGS. 2D and 3). The (GCG)7 polymorphism thus appears to be a modifier of severity of dominant OPMD. Furthermore, the (GCG)7 allele can act as a recessive mutation. This was documented in the French patient IX who inherited two copies of the (GCG)7 polymorphism and has a late-onset autosomal recessive form of OPMD (FIG. 2E). Case IX, who has a recessive form of OPMD, is shown to have inherited two copies of the (GCG)7 polymorphism.

This is the first description of short trinucleotide repeat expansions causing a human disease. The addition of only two GCG repeats is sufficient to cause dominant OPMD. OPMD expansions do not share the cardinal features of "dynamic mutations". The GCG expansions are not only short they are also meiotically quite stable. Furthermore, there is a clear cut-off between the normal and abnormal alleles, a single GCG expansion causing a recessive phenotype. The PAB II (GCG)7 allele is the first example of a relatively frequent allele which can act as either a modifier of a dominant phenotype or as a recessive mutation. This dosage effect is reminiscent of the one observed in a homozygote for two dominant synpolydactyly mutations. In this case, the patient had more severe deformities because she inherited two duplications causing an expansion in the polyalanine tract of the HOXD13 protein (Akarsu, A. N. et al., Hum. Mol. Genet. 5, 945-952 (1996)). A duplication causing a similar polyalanine expansion in the a subunit 1 gene of the core-binding transcription factor (CBF(1) has also been found to cause dominant cleido-cranial dysplasia (Mundlos, S. et al., Cell 89, 773-779 (1997)). The mutations in these two rare diseases are not triplet-repeats. The are duplications of "cryptic repeats" composed of mixed synonymous codons and are thought to result from unequal crossing over (Warren, S. T., Science 275, 408-409 (1997)). In the case of OPMD, slippage during replication causing a reiteration of the GCG codon is a more likely mechanism (Wells, D. R., J. Biol. Chem. 271, 2875-2878 (1996)).

Different observations converge to suggest that a gain of function of PAB II may cause the accumulation of nuclear filaments observed in OPMD (Tome, F.M.S. & Fardeau, Acta Neuropath. 49, 85-87 (1980)). PAB II is found mostly in dimeric and oligomeric forms (Nemeth, A. et al., Nucleic Acids Res. 23, 4034-4041 (1995)). It is possible that the polyalanine tract plays a role in polymerization. Polyalanine stretches have been found in many other nuclear proteins such as the HOX proteins, but their function is still unknown (Davies, S. W. et al., Cell 90, 537-548 (1997)). Alanine is a highly hydrophobic amino acid present in the cores of proteins. In dragline spider silk, polyalanine stretches are thought to form B-sheet structures important in ensuring the fibers' strength (Simmons, A. H. et al., Science 271, 84-87 (1996)). Polyalanine oligomers have also been shown to be extremely resistant to chemical denaturation and enzymatic degradation (Forood, B. et al., Bioch. and Biophy. Res. Com. 211, 7-13 (1995)). One can speculate that PAB II oligomers comprised of a sufficient number of mutated molecules might accumulate in the nuclei by forming undegradable polyalanine rich macromolecules. The rate of the accumulation would then depend on the ratio of mutated to non-mutated protein. The more severe phenotypes observed in homozygotes for the (GCG)9 mutations and compound heterozygotes for the (GCG)9 mutation and (GCG)7 allele may correspond to the fact that in these cases PAB II oligomers are composed only of mutated proteins. The ensuing faster filament accumulation could cause accelerated cell death. The recent description of nuclear filament inclusions in Huntington's disease, raises the possibility that "nuclear toxicity" caused by the accumulation of mutated homopolymeric domains is involved in the molecular pathophysiology of other triplet-repeat diseases (Davies, S. W. et al., Cell 90, 537-548 (1997); Scherzinger, E. et al., Cell 90, 549-558 (1997); DiFiglia, M. et al., Science 277, 1990-1993 (1997)). Future immunocytochemical and expression studies will be able to test this patho-physiological hypothesis and provide some insight into why certain muscle groups are more affected while all tissues express PAB II.

Methods

Contig and cDNA Selection

The cosmid contig was constructed by standard cosmid walking techniques using a gridded chromosome 14-specific cosmid library (Evans, G. A. et al., Gene 79, 9-20 (1989)). The cDNA clones were isolated by cDNA selection as previously described (Rommens, J. M. et al., in Proceedings of the third international workshop on the identification of transcribed sequences (eds. Hochgeschwender, U. & Gardiner, K.) 65-79 (Plenum, New York, 1994)).

Cloning of the PAB II Gene

Three cDNA clones corresponding to PAB II were sequenced (Sequenase, USB). Clones were verified to map to cosmids by Southern hybridization. The 8 kb HindIII restriction fragment was subcloned from cosmid 166G8 into pBluescriptII (SK) (Stratagene). The clone was sequenced using primers derived from the bPABII gene and human EST sequences. Sequencing of the PAB II introns was done by primer walking.

PAB II Mutation Screening and Sequencing

All cases were diagnosed as having OPMD on clinical grounds (Brais, B. et al., Hum. Mol. Genet. 4, 429-434 (1995)). RT-PCR- and genomic SSCP analyses were done using standard protocols (Lafrenière, R. G. et al., Nat. Genet. 15, 298-302 (1997)). The primers used to amplify the PAB II mutated region were: 5'-CGCAGTGCCCCGCCTTAGA-3' (SEQ ID NO:19) and 5'-ACAAGATGGCGCCGCCGC-CCCGGC-3' (SEQ ID NO:20). PCR reactions were performed in a total volume of 15 µl containing: 40 ng of genomic DNA; 1.5 µg of BSA; 1 µM of each primer; 250 µM dCTP and dTTP; 25 µM dATP; 125 µM of dGTP and 125 µM of 7-deaza-dGTP (Pharmacia); 7.5% DMSO; 3.75 µCi [$^{35}$S]dATP, 1.5 unit of Taq DNA polymerase and 1.5 mM MgCl2 (Perkin Elmer). For non-radioactive PCR reactions the [$^{35}$S]dATP was replaced by 225 µM of dATP. The amplification procedure consisted of an initial denaturation step at 95° C. for five minutes, followed by 35 cycles of denaturation at 95° C. for 15 s, annealing at 70° C. for 30 s, elongation at 74° C. for 30 s and a final elongation at 74° C. for 7 min. Samples were loaded on 5% polyacrylamide denaturing gels. Following electrophoresis, gels were dried and autoradiographs were obtained. Sizes of the inserts were determined by comparing to a standard M13 sequence (Sequenase™, USB). Fragments used for sequencing were gel-purified. Sequencing of the mutated fragment using the Amplicycle kit™ (Perkin Elmer) was done with the 5'-CG-CAGTGCCCCGCCTTAGAGGTG-3' (SEQ ID NO:21) primer at an elongation temperature of 68° C.

Stability of (GCG)-repeat Expansions

The meiotic stability of the (GCG)9-repeat was estimated based on a large French Canadian OPMD cohort. It had been previously established that a single ancestral OPMD carrier chromosome was introduced in the French Canadian population by three sisters in 1648. Seventy of the seventy one French Canadian OPMD families tested to date segregate a (GCG)9 expansion. However, in family F151, the affected brother and sister, despite sharing the French Canadian ancestral haplotype, carry a (GCG)12 expansion, twice the size of the ancestral (GCG)9 mutation (FIG. 2C). In this founder effect study, it is estimated that 450 (304-594) historical meioses shaped the 123 OPMD cases belonging to 42 of the 71 enrolled families. The screening of the full set of participants allowed an identification of another 148 (GCG)9 carrier chromosomes. Therefore, it is estimated that a single mutation of the (GCG)9 expansion has occurred in 598 (452-742) meioses.

Genotype-phenotype Correlations 176 carriers of at least one copy of the (GCG)9 mutation were examined during the early stage of the linkage study. All were asked to swallow 80 cc of ice-cold water as rapidly as possible. Testing was stopped after 60 seconds. The swallowing time (st) was validated as a sensitive test to identify OPMD cases (Brais, B. et al., Hum. Mol. Genet. 4, 429-434 (1995); Bouchard, J.-P. et al., Can. J. Neurol. Sci. 19, 296-297 (1992)). The st values for 76 (GCG)6 homozygotes normal controls is illustrated in FIG. 3. Analyses of variance were computed by two-way ANOVA (SYSTAT package). For the (GCG)9 homozygotes their mean st value was compared to the mean value for all (GCG)9 heterozygotes aged 35-40 ($P<10^{-5}$). For the (GCG)9 and (GCG)7 compound heterozygotes their mean st value was compared to the mean value for all (GCG)9 heterozygotes aged 45-65 ($P<10^{-5}$).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for the diagnosis or prognosis of oculopharyngeal muscular dystrophy (OPMD), a disease associated with protein accumulation in a cell nucleus, and/or swallowing difficulty and/or ptosis in a human patient, which comprises:
   a) determining allelic variants of a GCG repeat in exon I of the PAB II gene from a sample of said patient, said GCG repeat having the sequence $ATG(GCG)_{6+n}GCA$, wherein n is selected from 0 to 7, and
   whereby when at least one of the two alleles of said GCG repeat has an n equal to 1 to 7, said allele is associated with of OPMD, thereby diagnosing or prognosing OPMD in said human patient.

2. The method of claim 1, wherein n=0, and wherein said GCG repeat has the sequence set forth in SEQ ID NO:2.

3. The method of claim 1, wherein a first allele of said GCG repeat has an n which is equal to 1, and has the sequence set forth in SEQ ID NO:3.

4. The method of claim 1, wherein n is selected from 2 to 7, wherein said allelic variant is associated with an increased severity of said disease, and wherein said GCG repeat has the sequence selected from the group consisting of:
   a) SEQ ID NO:4, when n=2;
   b) SEQ ID NO:5, when n=3;
   c) SEQ ID NO:6, when n=4;
   d) SEQ ID NO:7, when n=5;
   e) SEQ ID NO:8, when n=6; and
   f) SEQ ID NO:9, when n=7.

5. The method of claim 3, wherein a second allele of said GCG repeat has an n selected from 2 to 7, said first allele is a modulator of the severity of the phenotype associated with said second allele, and wherein said GCG repeat of said second allele has the sequence selected from the group consisting of:
   a) SEQ ID NO:4, when n=2;
   b) SEQ ID NO:5, when n=3;
   c) SEQ ID NO:6, when n=4;
   d) SEQ ID NO:7, when n=5;
   e) SEQ ID NO:8, when n=6; and
   f) SEQ ID NO:9, when n=7.

6. A method of assessing a human sample for the presence or absence of an allelic variant of the PAB II gene that is associated with oculopharyngeal muscular dystrophy (OPMD), comprising:
   a) determining allelic variants of a GCG repeat in exon I of said PAB II gene from said sample, said GCG repeat having the sequence $ATG(GCG)_{6+n}GCA$, wherein n is selected from 0 to 7,
   whereby the presence of at least one of two alleles of said GCG repeat having n equal to 1 to 7 identifies the presence of an allelic variant of the PAB II gene associated with OPMD.

7. The method of claim 6, wherein the presence of two alleles of said GCG repeat having n=0, identifies the absence of an allelic variant of the PAB II gene that is associated with OPMD.

8. A method of assessing a human sample for the presence or absence of an allelic variant of the PAB II gene that is associated with oculopharyngeal muscular dystrophy (OPMD), comprising:
   a) determining allelic variants of a GCG repeat in exon I of said PAB II gene from said sample, said GCG repeat encoding the sequence:

$Met(Ala)_{6+n}Ala$, wherein n is selected from 0 to 7,
   whereby the presence of at least one of two alleles of said GCG repeat having n equal to 1 to 7 identifies the presence of an allelic variant of the PAB II gene associated with OPMD.

9. The method of claim 8, wherein the presence of two alleles of said GCG repeat having n=0, identifies the absence of an allelic variant of the PAB II gene that is associated with OPMD.

10. The method of claim 8, wherein a first allele of said GCG repeat has an n which is equal to 1.

11. The method of claim 10, wherein a second allele of said GCG repeat has an n selected from 2 to 7, and wherein said first allele is a modulator of the severity of the phenotype associated with said second allele.

* * * * *

```
                        SEQUENCE LISTING

<160> NUMBER OF SEQ ID NOS: 21

<210> SEQ ID NO 1
<211> LENGTH: 30
<212> TYPE: DNA
<213> ORGANISM: Homo sapiens

<400> SEQUENCE: 1
atggcggcgg cggcggcggc ggcagcagca                                    30

<210> SEQ ID NO 2
<211> LENGTH: 24
<212> TYPE: DNA
<213> ORGANISM: Homo sapiens

<400> SEQUENCE: 2
atggcggcgg cggcggcggc ggca                                          24

<210> SEQ ID NO 3
<211> LENGTH: 27
<212> TYPE: DNA
<213> ORGANISM: Homo sapiens

<400> SEQUENCE: 3
atggcggcgg cggcggcggc ggcggca                                       27

<210> SEQ ID NO 4
<211> LENGTH: 30
<212> TYPE: DNA
<213> ORGANISM: Homo sapiens

<400> SEQUENCE: 4
atggcggcgg cggcggcggc ggcggcggca                                    30

<210> SEQ ID NO 5
<211> LENGTH: 33
<212> TYPE: DNA
<213> ORGANISM: Homo sapiens

<400> SEQUENCE: 5
atggcggcgg cggcggcggc ggcggcggcg gca                                33
```

```
<210> SEQ ID NO 6
<211> LENGTH: 36
<212> TYPE: DNA
<213> ORGANISM: Homo sapiens

<400> SEQUENCE: 6
atggcggcgg cggcggcggc ggcggcggcg gcggca                        36

<210> SEQ ID NO 7
<211> LENGTH: 39
<212> TYPE: DNA
<213> ORGANISM: Homo sapiens

<400> SEQUENCE: 7
atggcggcgg cggcggcggc ggcggcggcg gcggcggca                     39

<210> SEQ ID NO 8
<211> LENGTH: 42
<212> TYPE: DNA
<213> ORGANISM: Homo sapiens

<400> SEQUENCE: 8
atggcggcgg cggcggcggc ggcggcggcg gcggcggcgg ca                 42

<210> SEQ ID NO 9
<211> LENGTH: 45
<212> TYPE: DNA
<213> ORGANISM: Homo sapiens

<400> SEQUENCE: 9
atggcggcgg cggcggcggc ggcggcggcg gcggcggcgg cggca              45

<210> SEQ ID NO 10
<211> LENGTH: 19
<212> TYPE: PRT
<213> ORGANISM: Homo sapiens

<400> SEQUENCE: 10

Met Ala Ala Ala Ala Ala Ala Ala Ala Ala Gly Ala Ala Gly Gly
 1               5                  10                  15

Arg Gly Ser

<210> SEQ ID NO 11
<211> LENGTH: 16
<212> TYPE: PRT
<213> ORGANISM: Homo sapiens

<400> SEQUENCE: 11

Met Ala Ala Ala Ala Ala Ala Ala Ala Ala Ala Gly Ala Ala Gly
 1               5                  10                  15

<210> SEQ ID NO 12
<211> LENGTH: 17
<212> TYPE: PRT
<213> ORGANISM: Homo sapiens

<400> SEQUENCE: 12

Met Ala Ala Ala Ala Ala Ala Ala Ala Ala Ala Ala Gly Ala Ala
 1               5                  10                  15

Gly

<210> SEQ ID NO 13
<211> LENGTH: 18
```

```
<212> TYPE: PRT
<213> ORGANISM: Homo sapiens

<400> SEQUENCE: 13

Met Ala Ala Ala Ala Ala Ala Ala Ala Ala Ala Ala Ala Gly Ala
 1               5                  10                  15

Ala Gly

<210> SEQ ID NO 14
<211> LENGTH: 19
<212> TYPE: PRT
<213> ORGANISM: Homo sapiens

<400> SEQUENCE: 14

Met Ala Ala Ala Ala Ala Ala Ala Ala Ala Ala Ala Ala Ala Gly
 1               5                  10                  15

Ala Ala Gly

<210> SEQ ID NO 15
<211> LENGTH: 20
<212> TYPE: PRT
<213> ORGANISM: Homo sapiens

<400> SEQUENCE: 15

Met Ala Ala Ala Ala Ala Ala Ala Ala Ala Ala Ala Ala Ala Ala
 1               5                  10                  15

Gly Ala Ala Gly
            20

<210> SEQ ID NO 16
<211> LENGTH: 21
<212> TYPE: PRT
<213> ORGANISM: Homo sapiens

<400> SEQUENCE: 16

Met Ala Ala Ala Ala Ala Ala Ala Ala Ala Ala Ala Ala Ala Ala
 1               5                  10                  15

Ala Gly Ala Ala Gly
            20

<210> SEQ ID NO 17
<211> LENGTH: 22
<212> TYPE: PRT
<213> ORGANISM: Homo sapiens

<400> SEQUENCE: 17

Met Ala Ala Ala Ala Ala Ala Ala Ala Ala Ala Ala Ala Ala Ala
 1               5                  10                  15

Ala Ala Gly Ala Ala Gly
            20

<210> SEQ ID NO 18
<211> LENGTH: 6002
<212> TYPE: DNA
<213> ORGANISM: Homo sapiens
<220> FEATURE:
<221> NAME/KEY: misc_feature
<222> LOCATION: (4616)...(4616)
<223> OTHER INFORMATION: n= A,T,C, or G

<400> SEQUENCE: 18
aatgaaggtg acacccaaa tagccccaat acaaatgcct gttcaatcaa ccaaacatct    60
```

-continued

| | |
|---|---|
| aagcagcaca tctatgtggt agcatattgc caggccgtga gactgcgaat ataaatagga | 120 |
| accgcccctc atctgcaggc gctcacaacc tagttagcaa acagtaaaac aattaagcgc | 180 |
| gccgtggaca taggcccact tgtcctggga aatgagggga agctgggggtt tgcagtggtt | 240 |
| tgattgaagg gggactacat gttagaggca cagactgggt gcaggtacac ccaaaggaac | 300 |
| gagaagagtg gaaggaaaca acatccacaa agtaaccaca tgctggcgta tcgaaggccg | 360 |
| tgatttacgg ttttgagact ttacctcgcc agcaaagggg ggccagtctg ttagcggtgc | 420 |
| agattggagg ggtgacattg gaagctgtcc aggaaaaaga aaatggaact ggggagcaga | 480 |
| aggcctacgc aagagggcgg gacagacagg acttgtgact agtagctctg gactgaggaa | 540 |
| tcctccctgc tttctggtgc gggagagcta gtggatgatg gtgccaataa cctggatggg | 600 |
| gaaagtaagc tccctcctgg aatgcttcat tcacaacctc cattttcagc aacatcccat | 660 |
| ctactggtgc ttcctggtcg agatacaagt ttcctgaaac tgctgctctg ttttgggcct | 720 |
| cacccggcca acagctcact agctggcaag cagtagtatc aagatggcgg ccccctagga | 780 |
| ctggctagtc atgtgacctc gggtttccca agtttgaagc ccggcagtcc tttcggggc | 840 |
| aaggttcacc tgtcacgaaa cgagtgtcac cccttcgact ctcgcaagcc aatcggcatc | 900 |
| tgagactggg ccactgcggt gaggcgatcg gaagattggt cctttccagt cgcctagcta | 960 |
| gggccaatca cggagcgtcc catacttcgc gggcccgccc gtaggccggg gagaagcagg | 1020 |
| aatatcgtca cagcgtggcg gtattattac ctaaggactc gataggaggt gggacgcgtg | 1080 |
| ttgattgaca ggcagatttc cctaccggga tttgagaatt tggcgcagtg cccgccttag | 1140 |
| aggtgcgctt atttgattgc caagtaatat tccccaatgg agtactagct catggtgacg | 1200 |
| ggcaggcagc ttgagctaat gagtcctccg tggccggcgc agctctccac atgccgggcg | 1260 |
| gcgggcccca gtctgagcgg cgatggcggc ggcggcggcg gcggcagcag cagcggggc | 1320 |
| tgcgggcggt cggggctccg ggccggggcg gcggcgccat cttgtgcccg gggccggtgg | 1380 |
| ggaggccggg gaggggcccc cggggggcgc aggggactac gggaacggcc tggagtctga | 1440 |
| ggaactggag cctgaggagc tgctgctgga gcccgagccg gagcccgagc ccgaagagga | 1500 |
| gccgccccgg ccccgcgccc cccgggagc tccgggccct gggcctggtt cgggagcccc | 1560 |
| cggcagccaa gaggaggagg aggagccggg actggtcgag ggtgaccgg gggacggcgc | 1620 |
| cattgaggac ccggtgagga aggagggcga gcgagcaggc cggcggctgg cgcgtcactg | 1680 |
| gaggcccaga gctcgggcga gcggtggcag gcggggggtg gggttgggcg gggaataacg | 1740 |
| tggctggggc gggtcgggcc ggggatgggt cagcgatcac tacaaggggc ccgactggct | 1800 |
| tgattcgggc gtcacggggtg cctagtgttg ttctagagag ggtagctttt cttttatcac | 1860 |
| gaccctcgca tggggcgagg gaaatggccg agcatggctg aggcgcgctc tggccgagag | 1920 |
| cagggcacag cccctgcgtt ggttcctctt aagctgtcct ccatacccctc cccacttata | 1980 |
| ttaggagctg gaagctatca aagctcgagt cagggagatg gaggaagaag ctgagaagct | 2040 |
| aaaggagcta cagaacgagg tagagaagca gatgaatatg agtccacctc caggcaatgc | 2100 |
| tgagtaactg gcggttgcac gcggagcccg ggttctcggg ttggaagggt tgtggggagg | 2160 |
| atggggaatg tggggttaga tactcggcac cctggagctg cttgtctgag ctattatgac | 2220 |
| tgtgccgcgc tcatagtccg ttgtgtgttc ctctgacctt tgtgaggcag aactgatatt | 2280 |
| ttggtggtgg tagccttgtg cctccctttg tcctgttata attgtgttgc tctttattct | 2340 |
| tagtctacgt ctatctttct ttggtagagg ttgcgtgctc gcatttgacc ttcaaatcta | 2400 |
| atagtttttc ctccaattgg agacgcttta ggattctaag agaaagcaag ctggaagggg | 2460 |

-continued

```
tttcccctttt aaattctaga aatgtggagt ctcagcccac ttaattttgc tcactcttaa   2520
aagcatttca accaaagcca ttcattaggg atttgatttg gagggcagga gggattccta   2580
tactgtttta agtgtgtatt aattctttca atttatcgaa ttatttagtg agtaacctgc   2640
tatgcactag gcactattct cggcttgtgg gtacagcagg gaacagcaca gaccaaaatc   2700
tttgccttca ctgagcttat gggatagtgc tggtggtgga agtgcaacat attggtcaag   2760
tagaaaacaa gtgtgtggtt tttgtaaaaa attatttttt cctgatagct ggcccggtga   2820
tcatgtccat tgaggagaag atggaggctg atgcccgttc catctatgtt ggcaatgtga   2880
cgtactgggg ctctgactgg ggttgggggc aagttcttct tttggggaat tatttaatag   2940
tcctgaaaga acatctccgg gatagatgtg gttttgggtg tggagggagt gtgggaagga   3000
ggttaaaggt aatggaatga tcagtaatca gcaaaggctc tgggtttgga aggaaaagag   3060
attaattcct caaattacca gatttcatgt gctttggtgt atgatggccc agaccaaagg   3120
ctcgggaggg ttcttttgag acaggaattt gcctggtgcc tgtgaaattt ttctcctctc   3180
atcaggtgga ctatggtgca acagcagaag agctggaagc tcactttcat ggctgtggtt   3240
cagtcaaccg tgttaccata ctgtgtgaca aatttagtgg ccatcccaaa ggtaaagtaa   3300 agggagtaa gttgagataa tttaaattac agtgtacaaa tagataaatt atgttttata   3360
ttgagcagta agttatttgg tgttaacaca ggtgatctgt gtcatttaag atcatggcat   3420
taatgttgat atatcaggag ttgcacctaa atgtcttcag aggccagata acaaaaatga   3480
aggctagatg tgggtgggat tacgaactag aaggggaggg gcagcttcta cttggcctat   3540
tatggcatat ggaaattcag gccctgtgtg tcttattttt acaaatttca aagagtagct   3600
ggaaatttta aaatttaaat gatttcgaat gattgaaatt ttccatttag aagaattttg   3660
acaaataaaa aatataactg cattgtagcc caaaacgaag catgcctgca ggttgaattt   3720
gacctgtgag gtatttgtaa cctcagagag atacaatgac aattcttttc aggtttgcgt   3780
atatagagtt ctcagacaaa gagtcagtga ggacttcctt ggccttagat gagtccctat   3840
ttagaggaag gcaaatcaag gtaagcctat gtccattgct gttctagttg tgtataaact   3900
ctccaggttg cctttaaggc tatcatttgt tcatctctga ctcaggtgat cccaaaacga   3960
accaacagac caggcatcag cacaacagac cggggttttc cacgagcccg ctaccgcgcc   4020
cggaccacca actacaacag ctcccgctct cgattctaca gtggttttaa cagcaggccc   4080
cggggtcgcg tctacaggtc aggatagatg ggctgctcct cttccccccg cctcccgtga   4140
gccccgtatg cttcctcctc tctggtctga ggaacctccc tccccccacc cctcccgtg   4200 gtcttcagga actttgtctc ctgcctgtgc aggttgagga aggtagttgc aggccaggcc   4260
agaaggcagc ctcatcatct tttctgcagt agaaattggt gataagggct gcatccctcc   4320
cttggttcaa agaggcttcc accccagcc ttttttttct tgggagttgg tggcatttga   4380
aggtgtttgc ggacaaaact gggaggaaca gggcctccag gaagttgaaa gcactgcttg   4440
gacatttgtt actttttcg gagttaggga gggattgaag actgaacctc ccttggaaga   4500
ataccagagg ctagctagtt gatcctccca acagccttgt gggaggattt tgagatactt   4560 attcttatt tgagccagtc ttgcaaggtt aacttctcac tgggcctagt gtggtnccca   4620 ggttttgcc ttgcttcact tctgtctcta catttaaata gacgggttag gcatataaac   4680
cttggctttt cataagctct acctgcctat cccaggagt tagggaggat ctatttgtga   4740
aggccctagg gtttaaaaac tgtggaggac tgaaaaactg gataaaaagg gggtccttt   4800
```

-continued

```
ccttgccect gtctctcact cagatgcgct tcttttcgc cactgtttgg caaagttttc      4860
tgttaagccc cctccccct gccccagttc tcccaggtgc gttactattt ctgggatcat      4920
ggggtcggtt ttaggacact tgaacacttc ttttcccccc ttcccttcac agtaactggg     4980
gcagggcct acggggaggg gcttgtactg aactatctag tgatcacgtt aacacctaac     5040
tctccttctt tcttccaggg gccgggctag agcgacatca tggtattccc cttactaaaa    5100
aaagtgtgta ttaggaggag agagaggaaa aaagaggaa agaaggaaaa aaaaaagaat     5160
taaaaaaaaa aaaagaaaa acagaagatg accttgatgg aaaaaaaata ttttttaaaa     5220
aaaagatata ctgtggaagg ggggagaatc ccataactaa ctgctgagga gggacctgct   5280
ttggggagta ggggaaggcc cagggagtgg ggcagggggc tgcttattca ctctggggat    5340
tcgccatgga cacgtctcaa ctgcgcaagc tgcttgccca tgtttccctg cccccttcac    5400
cccttgggc ctgctcaagg gtaggtgggc gtgggtggta ggagggtttt ttttacccag     5460
ggctctggaa ggacaccaaa ctgttctgct tgttaccttc cctcccgtct tctcctcgcc    5520
tttcacagtc ccctcctgcc tgctcctgtc cagccaggtc taccacccac cccacccctc    5580
tttctccggc tccctgcccc tccagattgc ctggtgatct attttgtttc cttttgtgtt    5640
tcttttctg ttttgagtgt ctttctttgc aggtttctgt agccggaaga tctccgttcc     5700
gctcccagcg gctccagtgt aaattcccct tcccctggg gaaatgcact accttgttt    5760
gggggtta ggggtgtttt tgttttcag ttgttttgtt ttttgtttt tttttttcc        5820
tttgccttt tccccttta tttggaggga atgggaggaa gtgggaacag ggaggtggga    5880
ggtggattt gtttattttt ttagctcatt tccaggggtg ggaatttttt tttaatatgt    5940
gtcatgaata aagttgtttt tgaaaataaa aaaaaaaaa aaaaaaaa aaaaaaaaa       6000
aa                                                                 6002

<210> SEQ ID NO 19
<211> LENGTH: 19
<212> TYPE: DNA
<213> ORGANISM: Artificial Sequence
<220> FEATURE:
<223> OTHER INFORMATION: oligonucleotide

<400> SEQUENCE: 19
cgcagtgccc cgccttaga                                                19

<210> SEQ ID NO 20
<211> LENGTH: 24
<212> TYPE: DNA
<213> ORGANISM: Artificial Sequence
<220> FEATURE:
<223> OTHER INFORMATION: oligonucleotide

<400> SEQUENCE: 20
acaagatggc gccgccgccc cggc                                          24

<210> SEQ ID NO 21
<211> LENGTH: 23
<212> TYPE: DNA
<213> ORGANISM: Artificial Sequence
<220> FEATURE:
<223> OTHER INFORMATION: oligonucleotide

<400> SEQUENCE: 21
cgcagtgccc cgccttagag gtg                                           23
```